United States Patent
Miller et al.

(10) Patent No.: US 10,882,030 B2
(45) Date of Patent: Jan. 5, 2021

(54) CRYSTALLINE TRANSITION METAL TUNGSTATE

(71) Applicant: UOP LLC, Des Plaines, IL (US)

(72) Inventors: Stuart R. Miller, Arlington Heights, IL (US); Susan C. Koster, Carpentersville, IL (US)

(73) Assignee: UOP LLC, Des Plaines, IL (US)

( * ) Notice: Subject to any disclaimer, the term of this patent is extended or adjusted under 35 U.S.C. 154(b) by 108 days.

(21) Appl. No.: 16/106,714

(22) Filed: Aug. 21, 2018

(65) Prior Publication Data

US 2019/0060882 A1    Feb. 28, 2019

Related U.S. Application Data (60) Provisional application No. 62/550,256, filed on Aug. 25, 2017.

(51) Int. Cl.
*B01J 23/888* (2006.01)
*G05B 15/02* (2006.01)
(Continued)

(52) U.S. Cl.
CPC .......... *B01J 23/888* (2013.01); *B01J 27/049* (2013.01); *B01J 37/0009* (2013.01); *B01J 37/009* (2013.01); *B01J 37/0018* (2013.01); *B01J 37/031* (2013.01); *B01J 37/033* (2013.01); *B01J 37/04* (2013.01); *B01J 37/06* (2013.01); *B01J 37/08* (2013.01); *B01J 37/20* (2013.01);
(Continued)

(58) Field of Classification Search
CPC .. B01J 23/888; B01J 37/0009; B01J 37/0018; B01J 37/009; B01J 37/031; B01J 37/033; B01J 37/04; B01J 37/06; B01J 37/08; B01J 37/20; B01J 2523/00; B01J 2523/69; B01J 2523/845; B01J 2523/847; C01P 2002/72; C01P 2002/74
USPC .................. 502/216, 219, 221, 305–313, 318
See application file for complete search history.

(56) References Cited

U.S. PATENT DOCUMENTS 2,529,546 A * 11/1950 Fallows ................ C01C 3/0204
                                                             423/373
2,556,255 A *  6/1951 Carosella .............. C01G 41/00
                                                             423/58
(Continued)

FOREIGN PATENT DOCUMENTS

CA   2719157 A1   10/2009
CA   2620656 C     3/2014
(Continued)

OTHER PUBLICATIONS

David L. Stern et al., "Propane Oxydehydrogenation over Metal Tungstates." Journal of Catalysis 167, pp. 570-572. (Year: 1997).*
(Continued)

*Primary Examiner* — Patricia L. Hailey (57) ABSTRACT

A hydroprocessing catalyst has been developed. The catalyst is a crystalline transition metal tungstate material or metal sulfides derived therefrom, or both. The hydroprocessing using the crystalline transition metal tungstate material may include hydrodenitrification, hydrodesulfurization, hydrodemetallation, hydrodesilication, hydrodearomatization, hydroisomerization, hydrotreating, hydrofining, and hydrocracking.

6 Claims, 1 Drawing Sheet

(51) Int. Cl.

| | | |
|---|---|---|
| *C10G 45/72* | (2006.01) | |
| *C10G 47/36* | (2006.01) | |
| *C10G 53/00* | (2006.01) | |
| *B01J 37/08* | (2006.01) | |
| *B01J 37/03* | (2006.01) | |
| *B01J 37/06* | (2006.01) | |
| *C01G 41/00* | (2006.01) | |
| *G16C 20/90* | (2019.01) | |
| *B01J 27/049* | (2006.01) | |
| *B01J 37/00* | (2006.01) | |
| *B01J 37/04* | (2006.01) | |
| *B01J 37/20* | (2006.01) | |
| *G16C 20/70* | (2019.01) | |
| *C01G 41/02* | (2006.01) | |
| *G16C 20/10* | (2019.01) | |
| *C10G 45/50* | (2006.01) | |
| *C01G 53/00* | (2006.01) | |

(52) U.S. Cl.
CPC ............ *C01G 41/00* (2013.01); *C01G 41/02* (2013.01); *C01G 53/00* (2013.01); *C01G 53/40* (2013.01); *C10G 45/72* (2013.01); *C10G 47/36* (2013.01); *G05B 15/02* (2013.01); *G16C 20/70* (2019.02); *G16C 20/90* (2019.02); *B01J 2523/00* (2013.01); *B01J 2523/69* (2013.01); *B01J 2523/845* (2013.01); *B01J 2523/847* (2013.01); *C01P 2002/72* (2013.01); *C01P 2002/74* (2013.01); *C10G 45/50* (2013.01); *G16C 20/10* (2019.02)

(56) References Cited

U.S. PATENT DOCUMENTS

| | | | |
|---|---|---|---|
| 3,306,840 A * | 2/1967 | Myers | C10G 67/04 208/87 |
| 3,549,518 A * | 12/1970 | Burgess | C10G 47/20 208/111.15 |
| 3,642,610 A * | 2/1972 | Divijak, Jr. | C10G 47/12 208/58 |
| 4,820,677 A | 4/1989 | Jacobson et al. | |
| 4,904,634 A | 2/1990 | Wieserman et al. | |
| 5,278,121 A | 1/1994 | Singhal et al. | |
| 6,156,695 A | 12/2000 | Soled et al. | |
| 6,162,350 A | 12/2000 | Soled et al. | |
| 6,197,273 B1 | 3/2001 | Nagano et al. | |
| 6,280,610 B1 | 8/2001 | Uragami et al. | |
| 6,299,760 B1 | 10/2001 | Soled et al. | |
| 6,534,437 B2 | 3/2003 | Eijsbouts et al. | |
| 6,582,590 B1 | 6/2003 | Riley et al. | |
| 6,620,313 B1 | 9/2003 | Demmin et al. | |
| 6,635,599 B1 | 10/2003 | Eijsbouts et al. | |
| 6,652,738 B2 | 11/2003 | Eijsbouts et al. | |
| 6,712,955 B1 | 3/2004 | Hou et al. | |
| 6,783,663 B1 | 8/2004 | Riley et al. | |
| 6,863,803 B1 | 3/2005 | Riley et al. | |
| 6,929,738 B1 | 8/2005 | Riley et al. | |
| 7,229,548 B2 | 6/2007 | Riley et al. | |
| 7,232,515 B1 | 6/2007 | Demmin et al. | |
| 7,232,934 B2 | 6/2007 | Saleh et al. | |
| 7,288,182 B1 | 10/2007 | Soled et al. | |
| 7,513,989 B1 | 4/2009 | Soled et al. | |
| 7,538,066 B2 | 5/2009 | Soled et al. | |
| 7,544,632 B2 | 6/2009 | Soled et al. | |
| 7,591,942 B2 | 9/2009 | Soled et al. | |
| 7,605,107 B2 | 10/2009 | Soled et al. | |
| 7,608,558 B2 | 10/2009 | Eijsbouts et al. | |
| 7,648,941 B2 | 1/2010 | Soled et al. | |
| 7,686,943 B2 | 3/2010 | Soled et al. | |
| 7,691,257 B2 | 4/2010 | Shih et al. | |
| 7,709,412 B2 | 5/2010 | Shih et al. | |
| 7,749,937 B2 | 7/2010 | Domokos et al. | |
| 7,776,205 B2 | 8/2010 | Soled et al. | |
| 7,780,845 B2 | 8/2010 | Soled et al. | |
| 7,951,746 B2 | 5/2011 | Bai et al. | |
| 8,062,508 B2 | 11/2011 | Soled et al. | |
| 8,067,331 B2 | 11/2011 | Eijsbouts-Spickova et al. | |
| 8,080,492 B2 | 12/2011 | Kuperman et al. | |
| 8,173,570 B2 | 5/2012 | Maesen et al. | |
| 8,206,575 B2 | 6/2012 | Maesen et al. | |
| 8,216,958 B2 | 7/2012 | Wu et al. | |
| 8,318,628 B2 | 11/2012 | Brun et al. | |
| 8,343,887 B2 | 1/2013 | Maesen et al. | |
| 8,377,289 B2 | 2/2013 | Li et al. | |
| 8,383,543 B2 | 2/2013 | Maesen et al. | |
| 8,586,500 B2 | 11/2013 | Kuperman et al. | |
| 8,636,967 B2 | 1/2014 | Canelon et al. | |
| 8,846,560 B2 | 9/2014 | Yang et al. | |
| 9,708,548 B2 * | 7/2017 | Soled | B01J 21/16 |
| 2003/0149323 A1 * | 8/2003 | Al-Zahrani | C07C 11/02 585/658 |
| 2007/0275845 A1 * | 11/2007 | Jansen | B01J 23/85 502/24 |
| 2008/0280754 A1 | 11/2008 | Toledo Antonio et al. | |
| 2009/0114566 A1 | 5/2009 | Chen et al. | |
| 2011/0052662 A1 * | 3/2011 | Nakano | C01G 41/02 424/443 |
| 2012/0065056 A1 | 3/2012 | Domokos et al. | |
| 2012/0122653 A1 | 5/2012 | Maesen et al. | |
| 2012/0122659 A1 | 5/2012 | Kuperman et al. | |
| 2012/0172199 A1 | 7/2012 | Yang et al. | |
| 2013/0068662 A1 | 3/2013 | Maesen et al. | |
| 2013/0178662 A1 * | 7/2013 | Zhou | B01J 23/88 568/885 |
| 2013/0337996 A1 | 12/2013 | Eijsbouts-Spickova et al. | |
| 2014/0027350 A1 | 1/2014 | Soled et al. | |
| 2015/0292095 A1 | 10/2015 | Haber et al. | |
| 2016/0121307 A1 * | 5/2016 | Jia | B01J 37/10 423/213.5 |
| 2017/0165644 A1 | 6/2017 | Miller et al. | |
| 2017/0165645 A1 | 6/2017 | Miller et al. | |
| 2017/0165646 A1 | 6/2017 | Miller et al. | |
| 2017/0165647 A1 | 6/2017 | Miller et al. | |
| 2017/0165648 A1 | 6/2017 | Miller et al. | |
| 2017/0165649 A1 | 6/2017 | Miller et al. | |
| 2017/0165650 A1 | 6/2017 | Miller et al. | |
| 2017/0165651 A1 | 6/2017 | Miller et al. | |
| 2017/0165652 A1 | 6/2017 | Miller et al. | |
| 2017/0165656 A1 | 6/2017 | Miller et al. | |
| 2017/0166605 A1 | 6/2017 | Miller et al. | |
| 2017/0218528 A1 | 8/2017 | Zhang et al. | |
| 2018/0169633 A1 | 6/2018 | Millet et al. | |
| 2019/0060873 A1 | 2/2019 | Millet et al. | |
| 2019/0185342 A1 * | 6/2019 | Miller | B01J 23/80 |
| 2019/0388875 A1 * | 12/2019 | Miller | B01J 27/049 |
| 2019/0388876 A1 * | 12/2019 | Miller | C01G 53/006 |
| 2019/0388877 A1 * | 12/2019 | Miller | B01J 23/8885 |
| 2019/0388879 A1 * | 12/2019 | Miller | C10G 45/08 |
| 2020/0001281 A1 * | 1/2020 | Miller | B01J 27/049 |
| 2020/0001282 A1 * | 1/2020 | Miller | B01J 23/007 |

FOREIGN PATENT DOCUMENTS

| | | |
|---|---|---|
| CN | 102049265 A | 5/2011 |
| EP | 2103347 A1 | 9/2009 |
| RU | 2098181 C1 | 12/1997 |
| WO | 200042126 A1 | 7/2000 |
| WO | 2009061295 A1 | 5/2009 |
| WO | 2014033653 A2 | 3/2014 |

OTHER PUBLICATIONS

Yanan Jiang et al., "A general strategy toward the rational synthesis of metal tungstate nanostructures using plasma electrolytic oxidaton method." Applied Surface Science 356, pp. 273-281. (Year: 2015).*

V. K. V. P. Srirapu et al., "Nanosized CoWO4 and NiWO4 as efficient oxygen-evolving electrocatalysts." Electrochimica Acta 209, pp. 75-84. (Year: 2016).*

(56) References Cited

OTHER PUBLICATIONS

Xiomara A. Lopez et al., "Synthesis, characterization and photocatalytic evaluation of MWO4 (M = Ni, Co, Cu and Mn) tungstates." International Journal of Hydrogen Energy 41, pp. 23312-23317. (Year: 2016).*

Jan Ungelenk et al., "Polyol-mediated low-temperature synthesis of crystalline tungstate nanoparticles MWO4 (M = Mn, Fe, Co, Ni, Cu, Zn)." Solid State Sciences 31, pp. 62-69. (Year: 2014).*

Amaya, "Unsupported sulfides obtained from high specific area mixed oxides as hydrotreating catalysts", Revista Facultad de Ingenieria, Universidad de Antioquia (2010), 56, 58-67, Language: Spanish, Database: CAPLUS.

An, "Preparation of unsupported and mesoporous Ni—Mo—W sulfide catalysts by low temperature solid-state reaction", Journal of China University of Petroleum (Edition of Natural Science), v 31, n 6, p. 156-160, Dec. 2007, ISSN: 16735005; Publisher: Ed. Off. Journal of the Univ. Petroleum, China. Language: Chinese.

Calderon-Magdaleno, "Effect of the amount of citric acid used in the preparation of NiMo/SBA-15 catalysts on their performance in HDS of dibenzothiophene-type compounds", Catalysis Today, v 220-222, p. 78-88, Mar. 2014; ISSN: 09205861; DOI: 10.1016/j.cattod.2013.06.002; Publisher: Elsevier.

Escobar, "Effect of ethylene glycol addition on the properties of P-doped NiMo/Al2O3 HDS catalysts: Part I. Materials preparation and characterization", Applied Catalysis B: Environmental, v 88, n. 3/4, p. 564-575, May 20, 2009; ISSN: 09263373; DOI: 10.1016/j.apcatb.2008.10.005; Publisher: Elsevier.

Gil-Llambias, "Hydrodesulfurization Catalysts Electrophoretic Study of Mo (or W)-Co, Mo (or W)-Ni, and Mo (Or W)-Ca Sulfided Phases", J. Catal., v 102, n 1, p. 37-42, Nov. 1986; ISSN: 00219517; Publisher: Academic Press.

Levin, "Crystal Structure of an Ammonium Nickel Molybdate Prepared by Chemical Precipitation", Inorg. Chem. 1996, 35, 4191-4197.

Nava, "Effect of phosphorus addition on unsupported Ni—Mo—W sulfide catalysts prepared by the in situ activation of nickel/tetramethylammonium thiomolybdotungstate", Applied Catalysis A: General, v 303, n 2, p. 177-184, Apr. 28, 2006; ISSN: 0926860X; DOI: 10.1016/j.apcata.2005.12.025; Publisher: Elsevier.

Nikulshin, "Influence of nature of precursors of aluminum nickel molybdenum catalysts on their performance in hydrodesulfurization", Neftekhimiya, v 46, n 5, p. 371-376, 2006; Language: Russian; ISSN: 00282421; Publisher: East View Publications.

Olivas, "Trimetallic NiMoW unsupported catalysts for HDS", ACS Division of Petroleum Chemistry, Inc. Preprints, v 50, n 4, p. 372-374, Aug. 2005; ISSN: 05693799; Publisher: American Chemical Society.

Yin, "A novel porous ammonium nickel molybdate as the catalyst precursor towards deep hydrodesulfurization of gas oil", p. 873-878, 2013, ISSN: 0016-2361, Publisher: Elsevier Science.

Yin, "Mechanism of Hydrodesulfurization of dibenzothiophenes on unsupported NiMoW catalyst", Journal of Fuel Chemistry and Technology, v 41, n 8, p. 991-997, Aug. 2013; ISSN: 18725813; DOI: 10.1016/S1872-5813(13) 60043-2; Publisher: Science Press.

Zhang, "Solution synthesis of unsupported Ni—W—S hydrotreating catalysts", Catalysis Communications 8 (2007) 2232-2237.

Zhou, "Study on hydrodesulfurization process of diesel on unsupported catalyst", Petroleum Processing and Petrochemicals, v 44, n 10, p. 38-43, Oct. 2013; Language: Chinese; ISSN: 10052399; Publisher: Research Institute of Petroleum Processing, SINOPEC.

Clearfield, "Studies in Heavy-Metal Molybdates. I. Crystal Structure of a Basic Zinc Molybdate, NaZn2OH(H20)(Mo04)21a", Inorganic Chemistry, vol. 15, No. 2, 1976, 335-338.

Clearfield, "Preparation and Structure of Manganese Molybdates", Inorg. Chem. 1985, 24, 4606-4609.

Clearfield, "Studies in Heavy-Metal Molybdates. 2. Crystal Structure of Disodium Di-u-hydroxo-dizin(II) Molybdate", Inorganic Chemistry, vol. 16, No. 3, 1977, 628-631.

Duan, "Ternary Ni—Co—Mo oxy-hydroxide nanoflakes grown on carbon cloth for excellent supercapacitor electrodes", Materials Letters 208 (2017) 65-68.

Hsu, "Synthesis and characterization of mesoporous Ni—Co oxyhydroxides for pseudocapacitor application", Electrochimica Acta 94 (2013) 104-112.

Lien, "High-performance asymmetric supercapacitor consisting of Ni—Co—Cu oxy-hydroxide nanosheets and activated carbon", Electrochemistry Communications 34 (2013) 323-326.

Xiao, "Remarkable improvement of the turn-on characteristics of a Fe2O3 photoanode for photoelectrochemical water splitting with coating a FeCoW oxy-hydroxide gel", Applied Catalysis B: Environmental 212 (2017) 89-96.

PCT/US2018/047750 International Search Report dated dated Dec. 13, 2018.

Xuan Li, Synthesis, characterizatio and catalystic testing of metal tungstates as catalysts for activation of lower alkanes. Doktor der Naturwissenschaften genehmigte Dissertation, Berlin 2017, Tag der wissenschaftlichen Asspjsche: Feb. 28, 2017.

Kannan S. et al. Effect of annealing on preparation of CuWO4 particles. Juniper Online Journal Material Science. 2017, 2(1): 555577, Submission Apr. 29, 2017; Published Jun. 23, 2017.

Xuan Li, Synthesis, characterization and catalytic testing of metal tungstates as catalysts for activation of lower alkanes, Doktor der Naturwissenschaften genehmigte Dissertation, Berlin, Feb. 28, 2017, p. 37, section 3, abstract, p. 49, section 3.4.1, p. 52, fig. S 3.2.

Kannan S. et al. Effect of annealing on prepartion of CuWO4 particles. Juniper Online Journal Material Science, 2017, 2(1):555577, Submission: Apr. 29, 2017; published: Jun. 23, 2017, abstract, figure 1 Experimental Procedure.

International Search Report and Written Opinion, PCT/US 2018/047750 (corresponding application), dated Dec. 13, 2018.

* cited by examiner

CRYSTALLINE TRANSITION METAL TUNGSTATE

CROSS-REFERENCE TO RELATED APPLICATION

This application claims priority from U.S. Provisional Application No. 62/550,256 filed Aug. 25, 2017, the contents of which cited application are hereby incorporated by reference in its entirety.

FIELD OF THE INVENTION

This invention relates to a new hydroprocessing catalyst. More particularly this invention relates to a crystalline transition metal tungstate and its use as a catalyst such as a hydrocarbon conversion catalyst or specifically a hydroprocessing catalyst. The hydroprocessing may include hydrodenitrification, hydrodesulfurization, hydrodemetallation, hydrodesilication, hydrodearomatization, hydroisomerization, hydrotreating, hydrofining, and hydrocracking.

BACKGROUND

In order to meet the growing demand for petroleum products there is greater utilization of sour crudes, which when combined with tighter environmental legislation regarding the concentration of nitrogen and sulfur within fuel, leads to accentuated refining problems. The removal of sulfur (hydrodesulfurization—HDS) and nitrogen (hydrodenitrification—HDN) containing compounds from fuel feed stocks is targeted during the hydrotreating steps of refining and is achieved by the conversion of organic nitrogen and sulfur to ammonia and hydrogen sulfide respectively.

Since the late 1940s the use of catalysts containing nickel (Ni) and molybdenum (Mo) or tungsten (W) have demonstrated up to 80% sulfur removal. See for example, V. N. Ipatieff, G. S. Monroe, R. E. Schaad, Division of Petroleum Chemistry, 115th Meeting ACS, San Francisco, 1949. For several decades now there has been an intense interest directed towards the development of materials to catalyze the deep desulfurization, in order to reduce the sulfur concentration to the ppm level. Some recent breakthroughs have focused on the development and application of more active and stable catalysts targeting the production of feeds for ultra low sulfur fuels. Several studies have demonstrated improved HDS and HDN activities through elimination of the support such as, for example, $Al_2O_3$. Using bulk unsupported materials provides a route to increase the active phase loading in the reactor as well as providing alternative chemistry to target these catalysts.

More recent research in this area has focused on the ultra deep desulfurization properties achieved by a Ni—Mo/W unsupported 'trimetallic' material reported in, for example, U.S. Pat. No. 6,156,695. The controlled synthesis of a broadly amorphous mixed metal oxide consisting of molybdenum, tungsten and nickel, significantly outperformed conventional hydrotreating catalysts. The structural chemistry of the tri-metallic mixed metal oxide material was likened to the hydrotalcite family of materials, referring to literature articles detailing the synthesis and characterization of a layered nickel molybdate material, stating that the partial substitution of molybdenum with tungsten leads to the production of a broadly amorphous phase which, upon decomposition by sulfidation, gives rise to superior hydrotreating activities.

The chemistry of these layered hydrotalcite-like materials was first reported by H. Pezerat, contribution à l'étude des molybdates hydrates de zinc, cobalt et nickel, C. R. ACAD. SCI., 261, 5490, who identified a series of phases having ideal formulas $MMoO_4 \cdot H_2O$, $EHM_2O^-(MoO_4)_2 \cdot H_2O$, and $E_{2-x}(H_3O)_xM_2O(MoO_4)_2$ where E can be $NH_4^+$, $Na^+$ or $K^+$ and M can be $Zn^{2+}$, $Co^{2+}$ or $Ni^{2+}$.

Pezerat assigned the different phases he observed as being Φc, Φy or Φy and determined the crystal structures for Φx and Φy, however owing to a combination of the small crystallite size, limited crystallographic capabilities and complex nature of the material, there were doubts raised as to the quality of the structural assessment of the materials. During the mid 1970s, Clearfield et al attempted a more detailed analysis of the Φx and Φy phases, see examples A. Clearfield, M. J. Sims, R. Gopal, INORG. CHEM., 15, 335; A. Clearfield, R. Gopal, C. H. Saldarriaga-Molina, INORG. CHEM., 16, 628. Single crystal studies on the product from a hydrothermal approach allowed confirmation of the Φx structure, however they failed in their attempts to synthesize Φy and instead synthesized an alternative phase, Na—Cu(OH)(MoO_4), see A. Clearfield, A. Moini, P. R. Rudolf, INORG. CHEM., 24, 4606.

The structure of Φy was not confirmed until 1996 when by Ying et al. Their investigation into a room temperature chimie douce synthesis technique in the pursuit of a layered ammonium zinc molybdate led to a metastable aluminum-substituted zincite phase, prepared by the calcination of Zn/Al layered double hydroxide $(Zn_4Al_2(OH)_{12}CO_3 \cdot zH_2O)$. See example D. Levin, S. L. Soled, J. Y. Ying, INORG. CHEM., 1996, 35, 4191-4197. This material was reacted with a solution of ammonium heptamolybdate at room temperature to produce a highly crystalline compound, the structure of which could not be determined through conventional ab-initio methods. The material was indexed, yielding crystallographic parameters which were the same as that of an ammonium nickel molybdate, reported by Astier, see example M. P. Astier, G. Dji, S. Teichner, J. ANN. CHIM. (PARIS), 1987, 12, 337, a material belonging to a family of ammonium-amine-nickel-molybdenum oxides closely related to Pezerat's materials. Astier did not publish any detailed structural data on this family of materials, leading to Ying et al reproducing the material to be analyzed by high resolution powder diffraction in order to elucidate the structure. Ying et al named this class of materials 'layered transition-metal molybdates' or LTMs.

SUMMARY OF THE INVENTION

A crystalline transition metal tungstate material has been produced and optionally sulfided, to yield an active hydroprocessing catalyst. The crystalline transition metal tungstate material has a unique x-ray powder diffraction pattern showing peaks at 6.2, 3.5 and 3.1 Å. The crystalline transition metal tungstate material has the formula:

$$MW_xO_y$$

where 'M' is a metal selected from Mn, Fe, Co, Ni, V, Cu, Zn, Sn, Sb, Ti, Zr, and mixtures thereof; 'x' varies from 0.35 to 2, or from 0.75 to 1.5, or from 0.8 to 1.2; 'y' is a number which satisfies the sum of the valency of M and W; the material is further characterized by a unique x-ray powder diffraction pattern showing peaks at the d-spacings listed in Table A:

TABLE A

| d (Å) | I/I₀ (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m |

Another embodiment involves a method of making a crystalline transition metal tungstate material having the formula:

$$MW_xO_y$$

where 'M' is a metal selected from Mn, Fe, Co, Ni, V, Cu, Zn, Sn, Sb, Ti, Zr and mixtures thereof; 'x' varies from 0.35 to 2, or from 0.75 to 1.5, or from 0.8 to 1.2; 'y' is a number which satisfies the sum of the valency of M and W; the material is further characterized by a unique x-ray powder diffraction pattern showing peaks at the d-spacings listed in Table A:

TABLE A

| d (Å) | I/I₀ (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m | wherein the method comprises: forming a reaction mixture containing water, source of M, source of W, and optionally a solubilizing agent, complexing agent, chelating agent, or a mixture thereof; optionally removing a component from the reaction mixture to generate an intermediate reaction mixture wherein the component is a precipitate, or at least a portion of the water, or both a precipitate and a portion of the water; reacting the reaction mixture or the intermediate mixture at a temperature from about 25° C. to about 500° C. for a period of time from about 30 minutes to 14 days to generate the crystalline transition metal tungstate material; and recovering the crystalline transition metal tungstate material.

Yet another embodiment involves a conversion process comprising contacting a sulfiding agent with a material to generate metal sulfides which are contacted with a feed at conversion conditions to generate at least one product, the material comprising: a crystalline transition metal tungstate material having the formula:

$$MW_xO_y$$

where 'M' is a metal selected from Mn, Fe, Co, Ni, V, Cu, Zn, Sn, Sb, Ti, Zr and mixtures thereof; 'x' varies from 0.35 to 2, or from 0.75 to 1.5, or from 0.8 to 1.2; 'y' is a number which satisfies the sum of the valency of M and W; the material is further characterized by a unique x-ray powder diffraction pattern showing peaks at the d-spacings listed in Table A:

TABLE A

| d (Å) | I/I0 (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m |

Additional features and advantages of the invention will be apparent from the description of the invention, FIGURE and claims provided herein.

DETAILED DESCRIPTION OF THE INVENTION

The present invention relates to a crystalline transition metal tungstate composition and a process for preparing the composition. The material has the designation UPM-18. This composition has an empirical formula:

$$MW_xO_y$$

where 'M' is a metal selected from Mn, Fe, Co, Ni, V, Cu, Zn, Sn, Sb, Ti, Zr and mixtures thereof; 'x' varies from 0.35 to 2, or from 0.75 to 1.5, or from 0.8 to 1.2; 'y' is a number which satisfies the sum of the valency of M and W.

The crystalline composition of the invention is characterized by having an extended network of M-O-M, where M represents a metal, or combination of metals listed above. The structural units repeat itself into at least two adjacent unit cells without termination of the bonding. The composition can have a one-dimensional network, such as, for example, linear chains.

The crystalline transition metal tungstate composition is further characterized by a unique x-ray powder diffraction pattern showing peaks at the d-spacings listed in Table A.

TABLE A

| d (Å) | I/I0 (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m |

Figure 1:
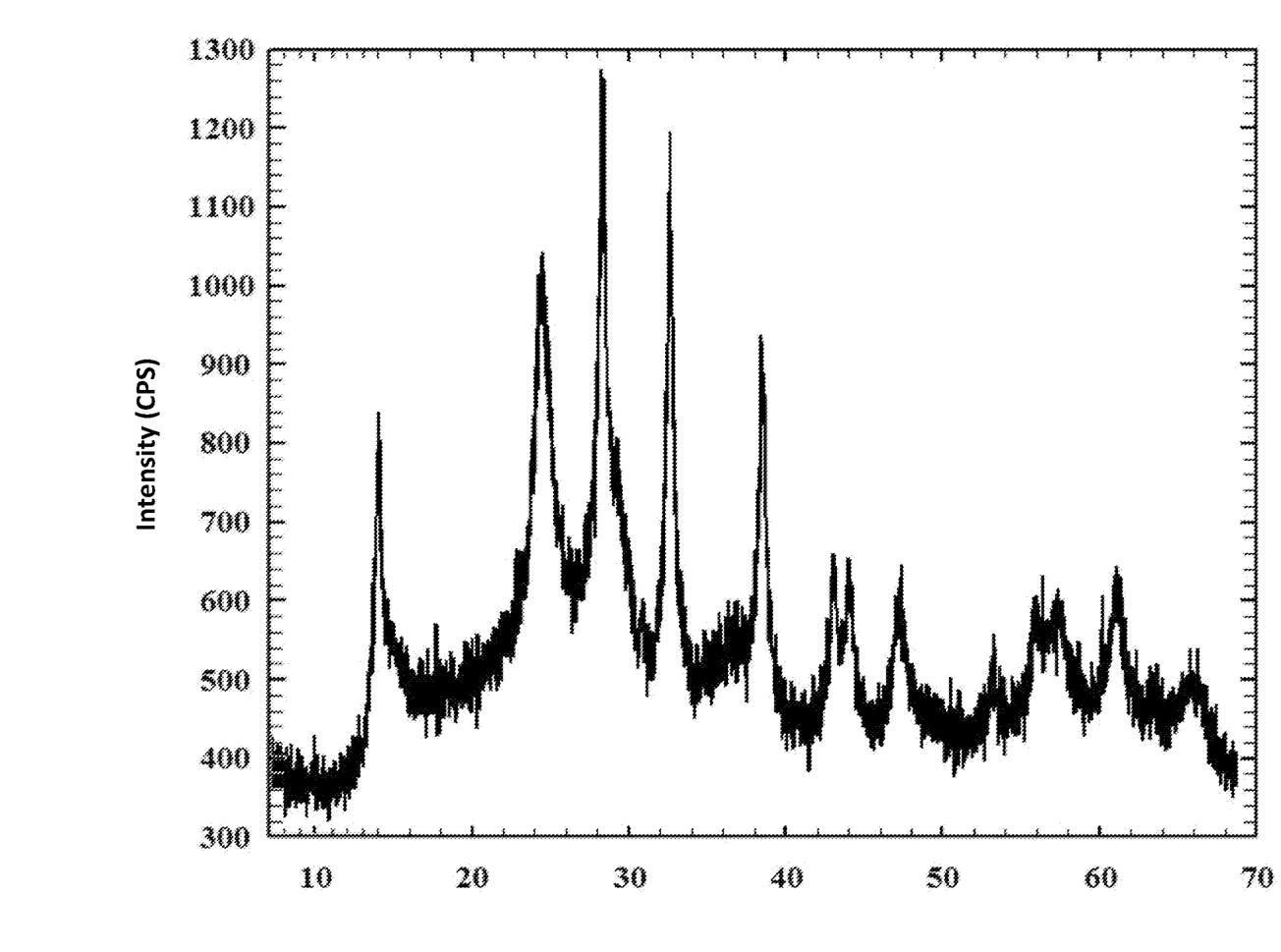
The FIGURE is the x-ray powder diffraction pattern of a crystalline transition metal tungstate prepared as described in the Examples.

The crystalline transition metal tungstate composition of the invention is yet further characterized by the x-ray powder diffraction pattern shown in the FIGURE.

The crystalline transition metal tungstate composition can be prepared by solvothermal crystallization of a reaction mixture, typically by mixing reactive sources of tungsten with the appropriate source of metal 'M'. Depending upon the metals sources selected, the reaction mixture may optionally include a solubilizing agent "SA" in order to facilitate the dissolution of the metals. The reaction mixture may also optionally include a complexing agent, a chelating agent, or both a complexing agent and a chelating agent "CA" in order to react with the metals prior to formation of the product.

Specific examples of the tungsten source which may be utilized in this invention include but are not limited to tungsten trioxide, ammonium ditungstate, ammonium thiotungstate, ammonium heptatungstate, ammonium paratungstate, tungstic acid, tungsten oxytetrachloride, tungsten hexachloride, hydrogen tungstate, sodium ditungstate, sodium metatungstate, sodium paratungstate, and ammonium metatungstate. Sources of other metals "M" include but are not limited to the respective halide, acetate, nitrate, carbonate, thiols and hydroxide salts. Specific examples include nickel chloride, cobalt chloride, nickel bromide, cobalt bromide, zinc chloride, copper chloride, iron chloride, magnesium chloride, magnesium chloride, nickel nitrate, cobalt nitrate, iron nitrate, manganese nitrate, zinc nitrate, copper nitrate, iron nitrate, nickel acetate, cobalt acetate, iron acetate, nickel carbonate, cobalt carbonate, zinc carbonate, manganese carbonate, copper carbonate, iron carbonate, nickel hydroxide, cobalt hydroxide, manganese hydroxide, copper hydroxide, zinc hydroxide, titanium oxide, manganese oxide, copper oxide, zinc oxide, cobalt oxide, nickel oxide, iron oxide, titanium tetrachloride, tin sulfate, zinc sulfate, iron sulfate, tin chloride pentahydrate, antimony chloride, antimony acetate, vanadium chloride.

Specific examples of the optional solubilizing agent "SA" include, but are not limited to, water, organic acids such as citric acid, malic acid, maleic acid, aliphatic acids; mineral acids such as sulfuric acid, hydrochloric acid, nitric acid, phosphoric acid and boric acid. Specific examples of the optional complexing or chelating agents include, but are not limited to, ammonium hydroxide, ammonium carbonate, ammonium bicarbonate, ammonium chloride, ammonium fluoride, ethylenediaminetetraacetic acid, ethylenedimaine, methylamine, dimethylamine or a combination thereof.

Generally, the solvothermal process used to prepare the composition of this invention involves forming a reaction mixture wherein all of the sources of the metal components, such as for example, Ni and W are mixed together, with the optional addition of either a solubilizing agent or a complexing agent or a chelating agent or any mixture thereof. The reaction may be at ambient temperatures or elevated temperatures. The pressure may be atmospheric pressure or autogenous pressure. The vessel used may be a closed vessel or an open vessel. Optionally, the mixture may be mixed, continuously or intermittently. In one embodiment, the reactants may be mixed intermittently at elevated temperatures. By way of specific examples, a reaction mixture may be formed which in terms of molar ratios of the oxides is expressed by the formula:

$$AMO_x:BWO_y:C(SA):D(CA):H_2O$$

where 'M' is selected from the group consisting of iron, cobalt, nickel, manganese, vanadium, copper, zinc and mixtures thereof; 'A' represents the molar ratio of 'M' and varies from 0.1 to 3 preferably from 0.5 to 2 or from 0.75 to 1.25; 'x' is a number which satisfies the valency of 'M'; 'B' represents the molar ratio of 'W' and varies from 0.1 to 3 preferably from 0.5 to 2 or from 0.75 to 1.25; 'y' is a number satisfies the valency of 'W'; 'C' represents the molar ratio of the optional solubilizing agent (SA) and varies from 0 to 50 or from 0.1 to 25 or from 1 to 10; 'D' represents the molar ratio of the optional complexing agent (CA) and varies from 0 to 100 or from 0.1 to 50 or from 5 to 20 the molar ratio of $H_2O$ and varies from 0.1 to 1000 or from 1 to 100 or from 2 to 20. If required, the starting reagents may be pretreated be either the addition of a complexing agent such as, but not limited to, ammonium hydroxide or citric acid. Depending upon the metal reagents selected, the pH of the mixture may be adjusted to an acidic or a basic regime. The pH of the mixture may be adjusted through the addition of a base such as $NH_4OH$, quaternary ammonium hydroxides, amines, and the like, or conversely be a mineral acid such as nitric acid, hydrochloric acid, sulfuric acid hydrofluoric acid, or an organic acid such as citric acid or malic acid, depending upon reactive sources of M. In one embodiment, the pH does not need to be adjusted.

In one embodiment, an intermediate reaction mixture may be formed by removing a component of the reaction mixture wherein the component is a precipitate, or at least a portion of the water, or both a precipitate and at least a portion of the water mixture. The intermediate may then then reacted as the reaction mixture at a temperature from about 25° C. to about 500° C. for a period of from about 30 minutes to 14 days to generate the crystalline transition metal tungstate material.

Once the reaction mixture is formed, the reaction mixture is reacted at temperatures ranging from about 25° C. to about 500° C. for a period of time ranging from 30 minutes to around 14 days. In one embodiment, the temperate range for the reaction is from about 300° C. to about 400° C. and in another embodiment the temperature is in the range of from about 100° C. to about 200° C. The temperature may be varied during the reaction period. In one embodiment, the reaction time is from about 4 to about 6 hours, and in another embodiment the reaction time is from about 4 to 7 days. The reaction is carried out under atmospheric pressure in an open vessel or in a sealed vessel under autogenous pressure. Optionally, the reaction mixture may be mixed continuously or intermittently. In one embodiment, the reaction mixture is mixed every few hours. The crystalline transition metal tungstate compositions are recovered as the reaction product. The crystalline transition metal tungstate compositions are characterized by their unique x-ray powder diffraction pattern as shown in Table A above and in the FIGURE.

Once formed, the crystalline transition metal tungstate composition may have a binder incorporated, where the binder may be, for example, silicas, aluminas, silica-aluminas, and mixtures thereof. The selection of binder includes but is not limited to, anionic and cationic clays such as hydrotalcites, pyroaurite-sjogrenite-hydrotalcites, montmorillonite and related clays, kaolin, sepiolites, silicas, aluminas such as (pseudo) boehomite, gibbsite, flash calcined gibbsite, eta-alumina, zicronica, titania, alumina coated titania, silica-alumina, silica coated alumina, alumina coated silicas and mixtures thereof, or other materials generally known as particle binders in order to maintain particle integrity. These binders may be applied with or without peptization. The binder may be added to the bulk crystalline transition metal tungstate composition, and the amount of binder may range from about 1 to about 30 wt % of the finished catalysts or from about 5 to about 26 wt % of the finished catalyst. The binder may be chemically bound to the crystalline transition metal tungstate composition, or may be present in a physical mixture with the crystalline transition metal tungstate composition.

At least a portion of the crystalline transition metal molybdotungstate composition, with or without a binder, or before or after inclusion of a binder, can be sulfided in situ in an application or pre-sulfided to form metal sulfides which in turn are used in an application as a catalyst. The sulfidation may be conducted under a variety of sulfidation conditions such as through contact of the crystalline transition metal molybdotungstate composition with a sulfiding agent such as sulfur-containing stream or feedstream, or a gaseous mixture of $H_2S/H_2$, or both. The sulfidation of the crystalline transition metal molybdotungstate composition may be performed at elevated temperatures, typically ranging from about 50° C. to about 600° C., or from about 150° C. to about 500° C., or from about 250° C. to about 450° C. The materials resulting from the sulfiding step, the decomposition products, are referred to as metal sulfides which can be used as catalysts in conversion processes. As noted above, at least a portion of the metal sulfides may be present in a mixture with at least one binder. The sulfiding step can take place at a location remote from other synthesis steps, remote from the location of the conversion process, or remote from both the location of synthesis and remote from location of the conversion process.

As discussed, at least a portion of the unsupported crystalline transition metal tungstate material can be sulfided and the resulting metal sulfides can be used as a catalyst or catalyst support in conversion processes such as hydrocarbon conversion processes. Hydroprocessing is one class of hydrocarbon conversion processes in which the crystalline transition metal tungstate material is useful as a catalyst. Examples of specific hydroprocessing processes are well known in the art and include hydrodenitrification, hydrodesulfurization, hydrodemetallation, hydrodesilication, hydrodearomatization, hydroisomerization, hydrotreating, hydrofining, and hydrocracking. In one embodiment, a conversion process comprises contacting the crystalline mixed transition metal tungstate with a sulfiding agent to generate metal sulfides which are contacted with a feed stream at conversion conditions to generate at least one product.

The operating conditions of the hydroprocessing processes listed above typically include reaction pressures from about 2.5 MPa to about 17.2 MPa, or in the range of about 5.5 to about 17.2 MPa, with reaction temperatures in the range of about 245° C. to about 440° C., or in the range of about 285° C. to about 425° C. Contact time for the feed and the active catalyst, referred to as liquid hour space velocities (LHSV), should be in the range of about 0.1 $h^{-1}$ to about 10 $h^{-1}$, or about 2.0 $h^{-1}$ to about 8.0 $h^{-1}$. Specific subsets of these ranges may be employed depending upon the feedstock being used. For example, when hydrotreating a typical diesel feedstock, operating conditions may include from about 3.5 MPa to about 8.6 MPa, from about 315° C. to about 410° C., from about 0.25/h to about 5/h, and from about 84 $Nm^3$ $H_2/m^3$ to about 850 $Nm^3$ $H_2/m^3$ feed. Other feedstocks may include gasoline, naphtha, kerosene, gas oils, distillates, and reformate.

Any of the lines, conduits, units, devices, vessels, surrounding environments, zones or similar used in the process or the method of making may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof, the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes or method described herein. Examples are provided below so that the invention may be described more completely. These examples are only by way of illustration and should not be interpreted as a limitation of the broad scope of the invention, which is set forth in the claims.

Patterns presented in the following examples were obtained using standard x-ray powder diffraction techniques. The radiation source was a high-intensity, x-ray tube operated at 45 kV and 35 mA. The diffraction pattern from the copper K-alpha radiation was obtained by appropriate computer based techniques. Powder samples were pressed flat into a plate and continuously scanned from 3° and 70° (2θ). Interplanar spacings (d) in Angstrom units were obtained from the position of the diffraction peaks expressed as θ, where θ is the Bragg angle as observed from digitized data. Intensities were determined from the integrated area of diffraction peaks after subtracting background, "Io" being the intensity of the strongest line or peak, and "I" being the intensity of each of the other peaks. As will be understood by those skilled in the art the determination of the parameter 2θ is subject to both human and mechanical error, which in combination can impose an uncertainty of about ±0.4° on each reported value of 2θ. This uncertainty is also translated to the reported values of the d-spacings, which are calculated from the 2θ values. In some of the x-ray patterns reported, the relative intensities of the d-spacings are indicated by the notations vs, s, m, and w, which represent very strong, strong, medium, and weak, respectively. In terms of 100(I/$I_0$), the above designations are defined as:

w=0.01-15,m=15-60:s=60-80and vs=80-100.

In certain instances, the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present. As will be understood to those skilled in the art, it is possible for different poorly crystalline materials to yield peaks at the same position. If a material is composed of multiple poorly crystalline materials, then the peak positions observed individually for each poorly crystalline material would be observed in the resulting summed diffraction pattern. Likewise, it is possible to have some peaks appear at the same positions within different, single phase, crystalline materials, which may be simply a reflection of a similar distance within the materials and not that the materials possess the same structure.

Example 1

Ammonium metatungstate hydrate (25.3 g, 0.1 moles of W) was dissolved in 150 ml of DI $H_2O$, concentrated ammonium hydroxide (25 mL, 30%) was added to this solution. A second solution was prepared by adding nickel nitrate hexahydrate (43.62 g, 0.15 moles of Ni) to 150 ml of DI $H_2O$. The two solutions were slowly mixed together over with the pH of the final solution being adjusted to pH 6.8 using a mild $HNO_3$ solution. The precipitate was isolated by filtration, washed with hot water and then heat treated for using a ramp rate of 2° C. per hour until the temperature reach 400° C. The material was kept at 400° C. for 24 hours. The resulting product was analyzed by X-ray powder diffraction, and the X-ray powder diffraction pattern is shown in the FIGURE.

Example 2

Using a ceramic dish, ammonium hydroxide (10 ml, 30%) was added to nickel carbonate hydrate (5.07 g, 0.05 moles of Ni) over a 30 minute period. Ammonium metatungstate hydrate (12.63 g, 0.05 moles of W) was added and the resultant mixture was mixed thoroughly and then heat treated for 12 hours at 150° C. with intermittent mixing. The mixture was then heat treated further at 350° C. for 24 hours. The resulting product was analyzed by X-ray powder diffraction, and the X-ray powder diffraction pattern is shown in the FIGURE.

Example 3

Using a ceramic dish, nickel nitrate hexahydrate (14.54 g, 0.05 moles of Ni), zinc nitrate hexahydrate (14.87 g, 0.05 moles of Zn) and ammonium metatungstate hydrate (17.71 g, 0.07 moles of W) were added together and the resultant mixture was mixed thoroughly before being heat treated for 12 hours at 150° C. with intermittent mixing. The mixture was then heat treated further at 350° C. for 24 hours. The resulting product was analyzed by X-ray powder diffraction, and the X-ray powder diffraction pattern is shown in the FIGURE.

Example 4

Using a ceramic dish, nickel nitrate hexahydrate (29.75 g, 0.1 moles of Ni) and ammonium metatungstate hydrate (17.71 g, 0.07 moles of W) were added together and the resultant mixture was mixed thoroughly before being heat treated for 12 hours at 150° C. with intermittent mixing. The mixture was then heat treated further at 400° C. for 24 hours. The resulting product was analyzed by X-ray powder diffraction, and the X-ray powder diffraction pattern is shown in the FIGURE.

Example 5

Using a ceramic dish, nickel nitrate hexahydrate (12.35 g, 0.042 moles of Ni), copper nitrate hemi(pentahydrate) (9.9 g, 0.043 moles of Cu) and ammonium metatungstate hydrate (17.71 g, 0.07 moles of W) were added together and the resultant mixture was mixed thoroughly before being heat treated for 1 hour at 75° C. The reaction intermediate was then mixed and heated at 85° C. for an hour before being heated at 110° C. for 12 hours. The sample was then ground to a fine powder and heat treated at 200° C. for 4 hours after which time the temperature was ramped at 2° C. $min^{-1}$, held at 300° C. for 4 hours and ramped again to 400° C. and held for a further 4 hours. The resulting product was analyzed by X-ray powder diffraction, and the X-ray powder diffraction pattern is shown in the FIGURE.

Example 6

Nickel nitrate hexahydrate (100 g, 0.34 moles of Ni), zinc nitrate (3.63 g, 0.03 moles of Zn), ammonium metatungstate hydrate (60.5 g, 0.24 moles of W) and ammonium carbonate (82.5 g, 0.86 moles) were mixed together in a covered beaker and heated at 50° C. for 4 days with intermittent mixing. The mixture was then transferred to a ceramic dish and heated at 70° C. for 1 day, before being heated to 120° C. The mixture was then heated for 1 hour at 10° C. intervals from 120° C. to 190° C., after which the material was heated at 200° C. for 24 hrs. The resulting product was analyzed by X-ray powder diffraction, and the X-ray powder diffraction pattern is shown in the FIGURE.

Specific Embodiments

Embodiment 1 is a crystalline transition metal tungstate material having the formula:

$MW_xO_y$ where 'M' is a metal selected from Mn, Fe, Co, Ni, V, Cu, Zn, Sn, Sb, Ti, Zr and mixtures thereof; 'x' varies from 0.35 to 2, 'y' is a number which satisfies the sum of the valency of M and W; the material is further characterized by a unique x-ray powder diffraction pattern showing peaks at the d-spacings listed in Table A:

TABLE A

| d (Å) | I/I0 (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m |

Another embodiment is the crystalline transition metal tungstate material of embodiment 1 wherein the crystalline transition metal tungstate material is present in a mixture with at least one binder and wherein the mixture comprises up to 25 wt % binder.

Another embodiment is any of the previous crystalline transition metal tungstate materials wherein the binder is selected from the group consisting of silicas, aluminas, silica-aluminas, and mixtures thereof.

Another embodiment is any of the previous crystalline transition metal tungstate materials wherein M is nickel or cobalt.

Another embodiment is any of the previous crystalline transition metal tungstate materials wherein M is nickel.

Another embodiment is any of the previous crystalline transition metal tungstate materials wherein the crystalline transition metal tungstate material is sulfided.

Embodiment 2 is a method of making a crystalline transition metal tungstate material having the formula:

$MW_xO_y$ where 'M' is a metal selected from Mn, Fe, Co, Ni, V, Cu, Zn, Sn, Sb, Ti, Zr and mixtures thereof; 'x' varies from 0.35 to 2; 'y' is a number which satisfies the sum of the valency of M and W; the material is further characterized by a unique x-ray powder diffraction pattern showing peaks at the d-spacings listed in Table A:

TABLE A

| d (Å) | I/I0 (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m | the method comprising: (a) forming a reaction mixture containing water, source of M, source of W, and optionally a solubilizing agent, complexing agent, chelating agent, or a mixture thereof; (b) optionally removing a component from the reaction mixture to generate an intermediate reaction mixture wherein the component is a precipitate, or at least a portion of the water, or both a precipitate and a portion of the water; (c) reacting the reaction mixture or the intermediate mixture at a temperature from about 25° C. to about 500° C. for a period of time from about 30 minutes to 14 days to generate the crystalline transition metal tungstate material; and (d) recovering the crystalline transition metal tungstate material.

Another embodiment is the method of embodiment 2 wherein the recovering is by filtration or centrifugation.

Another embodiment is any of the previous methods method of making the crystalline transition metal tungstate material further comprising adding a binder to the recovered crystalline transition metal tungstate material.

Another embodiment is any of the previous methods method of making the crystalline transition metal tungstate material wherein the binder is selected from the group consisting of aluminas, silicas, alumina-silicas, and mixtures thereof.

Another embodiment is any of the previous methods method of making the crystalline transition metal tungstate material further comprising sulfiding the recovered crystalline transition metal tungstate material.

Another embodiment is any of the previous methods method of making the crystalline transition metal tungstate material wherein the reacting is conducted under atmospheric pressure or autogenous pressure.

Another embodiment is any of the previous methods method of making the crystalline transition metal tungstate material further comprising intermittent mixing during the reacting.

Another embodiment is any of the previous methods method of making the crystalline transition metal tungstate material wherein the temperature is varied during the reacting.

Embodiment 3 is a conversion process comprising contacting a material with a sulfiding agent to convert at least a portion of the material to metal sulfides and contacting the metal sulfides with a feed at conversion conditions to generate at least one product, wherein the material comprises a crystalline transition metal tungstate material having the formula:

$MW_xO_y$ where 'M' is a metal selected from Mn, Fe, Co, Ni, V, Cu, Zn, Sn, Sb, Ti, Zr and mixtures thereof; 'x' varies from 0.35 to 2; 'y' is a number which satisfies the sum of the valency of M and W; the material is further characterized by a unique x-ray powder diffraction pattern showing peaks at the d-spacings listed in Table A:

TABLE A

| d (Å) | I/I0 (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m |

Another embodiment is embodiment 3 wherein the conversion process is hydroprocessing.

Another embodiment is any of the previous conversion processes wherein the conversion process is selected from the group consisting of hydrodenitrification, hydrodesulfurization, hydrodemetallation, hydrodesilication, hydrodearomatization, hydroisomerization, hydrotreating, hydrofining, and hydrocracking.

Another embodiment is any of the previous conversion processes wherein the crystalline transition metal tungstate material is present in a mixture with at least one binder and wherein the mixture comprises up to about 25 wt % binder.

Another embodiment is any of the previous conversion processes wherein the crystalline transition metal tungstate material is sulfided.

Another embodiment is embodiment 3 or 2 further comprising at least one of: sensing at least one parameter of the process or method and generating a signal or data from the sensing; or generating and transmitting a signal; or generating and transmitting data.

The invention claimed is:

1. A crystalline transition metal tungstate material having the formula:

$MW_xO_y$ where 'M' is a metal selected from Mn, Fe, Co, Ni, V, Cu, Zn, Sn, Sb, Ti, Zr and mixtures thereof; 'x' varies from 0.35 to 2; 'y' is a number which satisfies the sum of the valency of M and W; the material is further characterized by a unique x-ray powder diffraction pattern showing peaks at the d-spacings listed in Table A:

TABLE A

| d (Å) | I/I0 (%) |
|---|---|
| 6.20 | s |
| 3.52 | vs |
| 3.12 | vs |
| 2.74 | vs |
| 2.41 | s |
| 2.33 | s |
| 2.09 | vs |
| 1.93 | m | wherein, relative intensities of the d-spacings are indicated by the notations vs, s, and m, which represent very strong, strong, and medium, respectively.

2. The crystalline transition metal tungstate material of claim 1 wherein the crystalline transition metal tungstate material is present in a mixture with at least one binder and wherein the mixture comprises up to 25 wt % binder.

3. The crystalline transition metal tungstate material of claim 2 wherein the binder is selected from the group consisting of silicas, aluminas, silica-aluminas, and mixtures thereof.

4. The crystalline transition metal tungstate material of claim 1 wherein M is nickel or cobalt.

5. The crystalline transition metal tungstate material of claim 1 wherein M is nickel.

6. The crystalline transition metal tungstate material of claim 1 wherein the crystalline transition metal tungstate material is sulfided.

\* \* \* \* \*